United States Patent
Wong et al.

(10) Patent No.: US 9,014,851 B2
(45) Date of Patent: Apr. 21, 2015

(54) SYSTEMS AND METHODS FOR TRACKING ROBOTICALLY CONTROLLED MEDICAL INSTRUMENTS

(71) Applicant: Hansen Medical, Inc., Mountain View, CA (US)

(72) Inventors: Serena Wong, Mountain View, CA (US); Sean Walker, Mountain View, CA (US); Jason Hsu, Mountain View, CA (US); June Park, Palo Alto, CA (US); Neal Tanner, Mountain View, CA (US); Kiran Murthy, Sunnyvale, CA (US)

(73) Assignee: Hansen Medical, Inc., Mountain View, CA (US)

( * ) Notice: Subject to any disclaimer, the term of this patent is extended or adjusted under 35 U.S.C. 154(b) by 119 days.

(21) Appl. No.: 13/835,698

(22) Filed: Mar. 15, 2013

(65) Prior Publication Data
US 2014/0276937 A1    Sep. 18, 2014

(51) Int. Cl.
| | |
|---|---|
| A61B 5/00 | (2006.01) |
| A61B 19/00 | (2006.01) |
| A61B 8/12 | (2006.01) |
| A61B 17/00 | (2006.01) |

(52) U.S. Cl.
CPC ....... *A61B 17/00* (2013.01); *A61B 2017/00212* (2013.01)

(58) Field of Classification Search
USPC ............. 600/407, 104, 423, 167, 1, 114, 424, 600/439, 478, 117; 601/1; 700/245
See application file for complete search history.

(56) References Cited

U.S. PATENT DOCUMENTS

| | | |
|---|---|---|
| 5,398,691 A | 3/1995 | Martin et al. |
| 5,408,409 A | 4/1995 | Glassman et al. |
| 5,524,180 A | 6/1996 | Wang et al. |
| 5,553,611 A | 9/1996 | Budd et al. |
| 5,558,091 A | 9/1996 | Acker et al. |
| 5,631,973 A | 5/1997 | Green |
| 5,636,255 A | 6/1997 | Ellis |
| 5,713,946 A | 2/1998 | Ben-Haim |
| 5,729,129 A | 3/1998 | Acker |
| 5,749,362 A | 5/1998 | Funda et al. |
| 5,859,934 A | 1/1999 | Green |
| 5,873,822 A | 2/1999 | Ferre et al. |
| 5,876,325 A | 3/1999 | Mizuno et al. |
| 5,902,239 A | 5/1999 | Buurman |
| 5,920,319 A | 7/1999 | Vining et al. |
| 5,951,475 A | 9/1999 | Gueziec et al. |
| 6,016,439 A | 1/2000 | Acker |
| 6,019,724 A | 2/2000 | Gronningsaeter et al. |
| 6,226,543 B1 | 5/2001 | Gilboa et al. |
| 6,233,476 B1 | 5/2001 | Strommer et al. |
| 6,253,770 B1 | 7/2001 | Acker et al. |
| 6,259,806 B1 | 7/2001 | Green |
| 6,272,371 B1 | 8/2001 | Shlomo |
| 6,424,885 B1 | 7/2002 | Niemeyer et al. |
| 6,592,520 B1 | 7/2003 | Peszynski |
| 6,593,884 B1 | 7/2003 | Gilboa et al. |
| 6,711,429 B1 | 3/2004 | Gilboa et al. |

(Continued)

FOREIGN PATENT DOCUMENTS

WO    03086190 A1    10/2003

*Primary Examiner* — Ronnie Mancho
(74) *Attorney, Agent, or Firm* — Scott M. Smith; Dorsey & Whitney LLP

(57) ABSTRACT

Systems and methods are described herein for tracking an elongate instrument or other medical instrument in an image.

51 Claims, 4 Drawing Sheets

(56) References Cited

U.S. PATENT DOCUMENTS

| | | | |
|---|---|---|---|
| 6,726,675 B1 | 4/2004 | Beyar | |
| 6,782,287 B2 | 8/2004 | Grzeszczuk et al. | |
| 6,892,090 B2 | 5/2005 | Verard et al. | |
| 6,994,094 B2 | 2/2006 | Schwartz | |
| 6,996,430 B1 | 2/2006 | Gilboa et al. | |
| 7,155,315 B2 | 12/2006 | Niemeyer et al. | |
| 8,287,522 B2* | 10/2012 | Moses et al. | 606/1 |
| 8,460,236 B2 | 6/2013 | Roelle et al. | |
| 8,600,551 B2* | 12/2013 | Itkowitz et al. | 700/245 |
| 8,821,376 B2* | 9/2014 | Tolkowsky | 600/104 |
| 2005/0033149 A1 | 2/2005 | Strommer et al. | |
| 2005/0171508 A1 | 8/2005 | Gilboa | |
| 2005/0267359 A1* | 12/2005 | Hussaini et al. | 600/423 |
| 2006/0020279 A1* | 1/2006 | Chauhan et al. | 606/167 |
| 2006/0025676 A1 | 2/2006 | Viswanathan et al. | |
| 2006/0076023 A1 | 4/2006 | Rapacki et al. | |
| 2006/0089624 A1* | 4/2006 | Voegele et al. | 606/1 |
| 2006/0184016 A1 | 8/2006 | Glossop | |
| 2007/0013336 A1 | 1/2007 | Nowlin et al. | |
| 2007/0015997 A1 | 1/2007 | Higgins et al. | |
| 2007/0055128 A1 | 3/2007 | Glossop | |
| 2007/0060790 A1* | 3/2007 | Kura et al. | 600/114 |
| 2007/0078334 A1* | 4/2007 | Scully et al. | 600/424 |
| 2007/0135803 A1 | 6/2007 | Belson | |
| 2007/0197896 A1* | 8/2007 | Moll et al. | 600/407 |
| 2007/0225559 A1 | 9/2007 | Clerc et al. | |
| 2007/0265503 A1 | 11/2007 | Schlesinger et al. | |
| 2007/0276180 A1 | 11/2007 | Greenburg et al. | |
| 2007/0293721 A1 | 12/2007 | Gilboa | |
| 2008/0212082 A1 | 9/2008 | Froggatt et al. | |
| 2009/0137952 A1 | 5/2009 | Ramamurthy et al. | |
| 2009/0262109 A1 | 10/2009 | Markowitz et al. | |
| 2010/0185087 A1* | 7/2010 | Nields et al. | 600/439 |

* cited by examiner

SYSTEMS AND METHODS FOR TRACKING ROBOTICALLY CONTROLLED MEDICAL INSTRUMENTS

TECHNICAL FIELD

The disclosure relates generally to medical instruments, such as elongate steerable instruments for minimally-invasive intervention or diagnosis, and more particularly to methods, systems, and apparatus for controlling or tracking the location, position, orientation or shape of one or more parts of a medical instrument using registration techniques.

BACKGROUND

Currently known minimally invasive procedures for diagnosis and treatment of medical conditions use shapeable instruments, such as steerable devices, flexible catheters or more rigid arms or shafts, to approach and address various tissue structures within the body. For various reasons, it is highly valuable to be able to determine the 3-dimensional spatial position of portions of such shapeable instruments relative to other structures, such as the operating table, other instruments, or pertinent anatomical tissue structures. Such information can be used for a variety of reasons, including, but not limited to: improve device control; to improve mapping of the region; to adapt control system parameters (whether kinematic and/or solid mechanic parameters); to estimate, plan and/or control reaction forces of the device upon the anatomy; and/or to even monitor the system characteristics for determination of mechanical problems. Alternatively, or in combination, shape information can be useful to simply visualize the tool with respect to the anatomy or other regions whether real or virtual.

In many conventional systems, the catheter (or other shapeable instrument) is controlled in an open-loop manner, as described in U.S. patent Ser. No. 12/822,876, the contents of which are incorporated by reference in its entirety. However, at times the assumed motion of the catheter does not match the actual motion of the catheter. One such reason for this issue is the presence of unanticipated or unmodeled constraints imposed by the patient's anatomy.

Thus to perform certain desired applications, such as, for example, instinctive driving, shape feedback, and driving in a fluoroscopy view or a model, there exists a need for tool sensors to be properly registered to the patient in real time. Moreover, there remains a need to apply the information gained by spatial information or shape and applying this information to produce improved device control or improved modeling when directing a robotic or similar device. There also remains a need to apply such controls to medical procedures and equipment.

SUMMARY

A robotic system for manipulating a tool with respect to a target space is disclosed herein. The tool comprises a sensor coupled thereto. The system comprises a robotic drive system and a controller. The robotic drive system comprises at least one actuator and is configured to couple with the tool to position the tool with respect to the target space. The controller is configured to use a registration between a sensor frame and a target space frame such that the controller can direct the robotic drive system in the target space frame using the registration. In some exemplary arrangements, the controller is configured to combine a plurality of discrete registrations to produce a combined registration between the sensor frame and the target space frame.

Other and further exemplary configurations and advantages thereof will become apparent from the following detailed description when read in view of the accompanying figures.

DETAILED DESCRIPTION

Figure 1A:
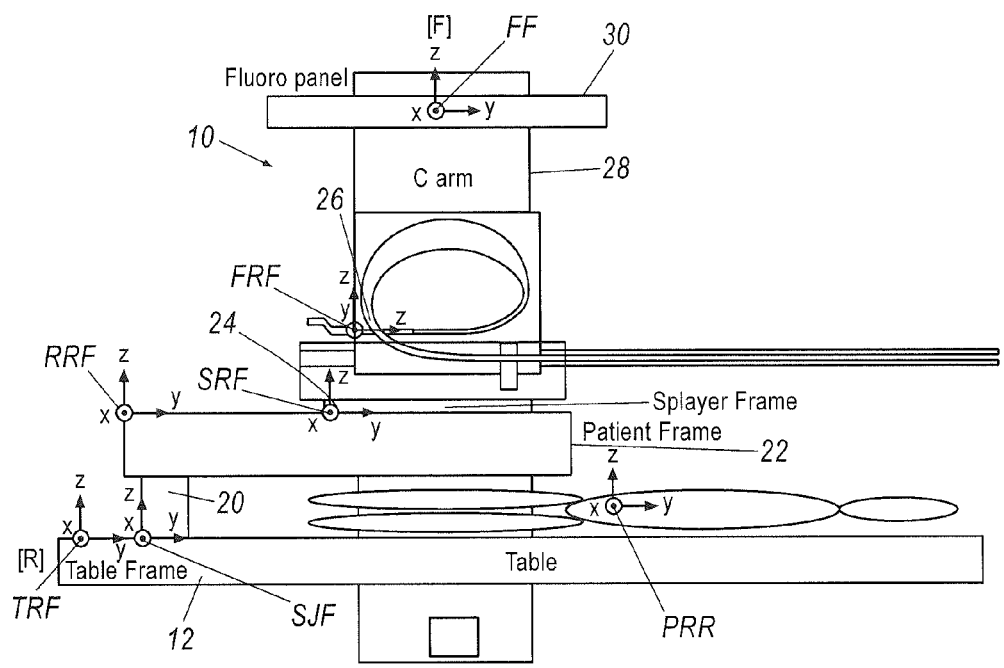
FIG. 1A illustrates a variation of a localization system in a typical operation room set up.

Various localization systems and methods for tracking an elongate instrument or tool, e.g., a robotically controlled elongate instrument, in real time, in a clinical or other environment, are described herein. The term "localization" is used in the art in reference to systems for determining and/or monitoring the position of objects, such as medical instruments or tools in a reference coordinate system. Various instruments are contemplated for use in the various systems described herein. In one exemplary arrangement, elongate instruments are contemplated, such as, e.g., a catheter or vascular catheter. The various methods and systems may include integrating or registering a localization system or a localization sensor coupled to a surgical tool, with an image. A fiber optic tracking or localization system is just one, non-limiting example of a system that allows for the tracking of a location, position and/or orientation of a localization sensor placed. Various other localization sensors may be utilized, e.g., electromagnetic sensors, and other sensors for detecting or controlling the movement of medical equipment. When the localization sensor is integrated into an image, it enhances the capabilities of an instrument control or tracking system by allowing a user or doctor to easily navigate the instrument through the complex anatomy without exposing the patient to excessive radiation over a prolonged period of time.

The localization data or tracking information of a localization sensor may be registered to the desired image or model to allow for navigation of an elongate instrument through the image or model to accurately represent movement of the elongate instrument within a patient. Registration is a process that requires relating a reference frame of a sensor to another reference frame of interest. If the positions, orientations or shapes of two or more objects are known in the same reference frame, then the actual positions, orientations or shapes of each object relative to each other may be ascertained. Thus, with this information, one can drive or manipulate one of the objects relative to the other objects.

In most interventional procedures, the reference frame of interest is the visualization frame. The reference frame is the frame that the doctor is viewing, such as a patient or a live 2D/3D image such fluoroscopy, ultrasound or others. Thus, the goal of registration is to determine the relationship of a frame of a sensor integrated into a tool or element in the surgical suite within the frame of reference of the patient, as represented in a 2D/3D image.

When the tool is registered to a 3D model, the user can drive and manipulate the tool in the 3D model. This technique provides an advantage in that there is no longer a need for live fluoroscopy and radiation during a procedure. The tool is localized to the 3D model and the position, shape and orientation of the tool is visible to the user. Since the tool position, shape and orientation is updated real time by a localization sensor, an image of the tool in the virtual representation of the 3D model will be updated as it is being advanced into the patient. The sensor is localized to the reference frame of the 3D model; therefore the orientation of a tip of the tool is known relative to the 3D model. This enables driving of the tool (such as a catheter) with 3 dimensional views of the anatomy and hence improves visualization and control during a surgical procedure.

However, many localization sensors are incremental measurement sensors, where the position and orientation of a particular point is calculated and dependent on the previously calculated orientation and positions/point spacings. Thus, the localization sensor operating in any medical system needs to be registered with a coordinate system, frame or image that is useful to an operator, such as the pre-operative 3D model or a fluoroscopic image. For incremental measurement sensors, such registration is challenging because the coordinate system or frame of the sensor is not always easily related to the coordinate system of interest (i.e., the pre-operative 3D model).

Moreover, the relationship between the sensor and the coordinate system of the interest may change over time during a procedure. For example, in one exemplary robotic system, a fiber optic sensor may have its reference frame based physically in a splayer for a catheter. Thus, as the splayer is robotically driven during a surgical procedure, the position and orientation of the bases of the fiber will change with respect to other reference frames.

In addition to changing positions of reference frames, the registration process often requires information about the imaging system providing the image, such as its physical dimensions and/or the details about the imaging techniques used to acquire a particular 3D model or other image. Due to the variability in equipment used in a clinical environment, in certain situations there may be no guarantee that such information will be available or easily obtainable to an outside party.

As such, various techniques to estimate system parameters and various registration techniques may help facilitate the clinical use of localization technology.

In certain variations, a method for tracking a robotically controlled elongate instrument in real time may include displaying an image of a patient's anatomy. A localization sensor may then be coupled to the robotically controlled instrument. The localization sensor may provide localization data of the sensor and/or instrument. Moreover, different sensors may be registered to specific tools, thereby enabling tool differentiation. The localization data from the localization sensor may be registered to the image. Registering may include transforming localization data generated by the localization sensor to the coordinate system or frame of the image such that localization data of the elongate instrument, to which the localization sensor is coupled, is overlaid on the image. The coordinate system of the localization sensor may be transformed or translated to the coordinate system of the image through one or more transformations, and optionally through other coordinate systems, to register the localization data to the image. As a result, a continuously or substantially continuously updated location of at least a portion of the elongate instrument is provided in the image of the anatomy of a patient, which allows for or facilitates robotic navigation or control of the elongate instrument through the anatomy e.g., through the vasculature of a patient.

The location, position and/or orientation of the localization sensor may be continuously tracked to allow for accurate manipulation of the elongate instrument in or through the anatomy of a patient. Various types of images may be utilized in the methods and systems described herein. For example, an image may be generated by CT or 2D or 3D fluoroscopy. An image may include a 3D or 2D anatomical model or a 2D or 3D fluoroscopic image or other types of images useful for visualizing an anatomy of a patient to perform various medical procedures.

When using a fluoroscopy image, an image intensifier may be utilized. Localization data from the localization sensor may be registered to a fluoroscopy coordinate system of a fluoroscopy image coupled to the image intensifier. In order to register the localization data from the localization sensor to the fluoroscopy image, various parameters may be ascertained or known. For example, such parameters may include: a distance from an X-ray source to the image intensifier, a distance from the source to a bed, a size of the image intensifier, and/or the axis of rotation of a C-arm of the fluoroscopy system.

In certain variations, localization data can be registered to a 3D anatomical model or a fluoroscopy image. The techniques used to perform the registration vary depending on the target. Where localization data is registered to a fluoroscopy image, the 2D nature of the fluoroscopy images may require that multiple images be taken at different angles before the registration process is complete.

FIG. 1A is a schematic of a typical operation room set up for a robotic surgical system. More specifically, a typical robotic surgical system 10 includes a table 12 upon which a patient 14 will be placed, a fluoroscopy system 16, and a surgical tool, such as a catheter 18 (best seen in FIG. 2). Attached to the table 12 is a setup joint arm 20 to which a remote catheter manipulator (RCM) 22 is operatively connected. A splayer 24 may be mounted to the RCM 22. A surgical tool, such as a catheter, is operatively connected to the splayer 24. A fiber sensor 26 may be operatively connected to the surgical tool. The fluoroscopy system 16 includes a C-arm 28. A fluoroscopy panel 30 is mounted to the C-arm 28. The C-arm is selectively moveable during the procedure to permit various images of the patient to be taken by the fluoroscopy panel 30.

Figure 2:
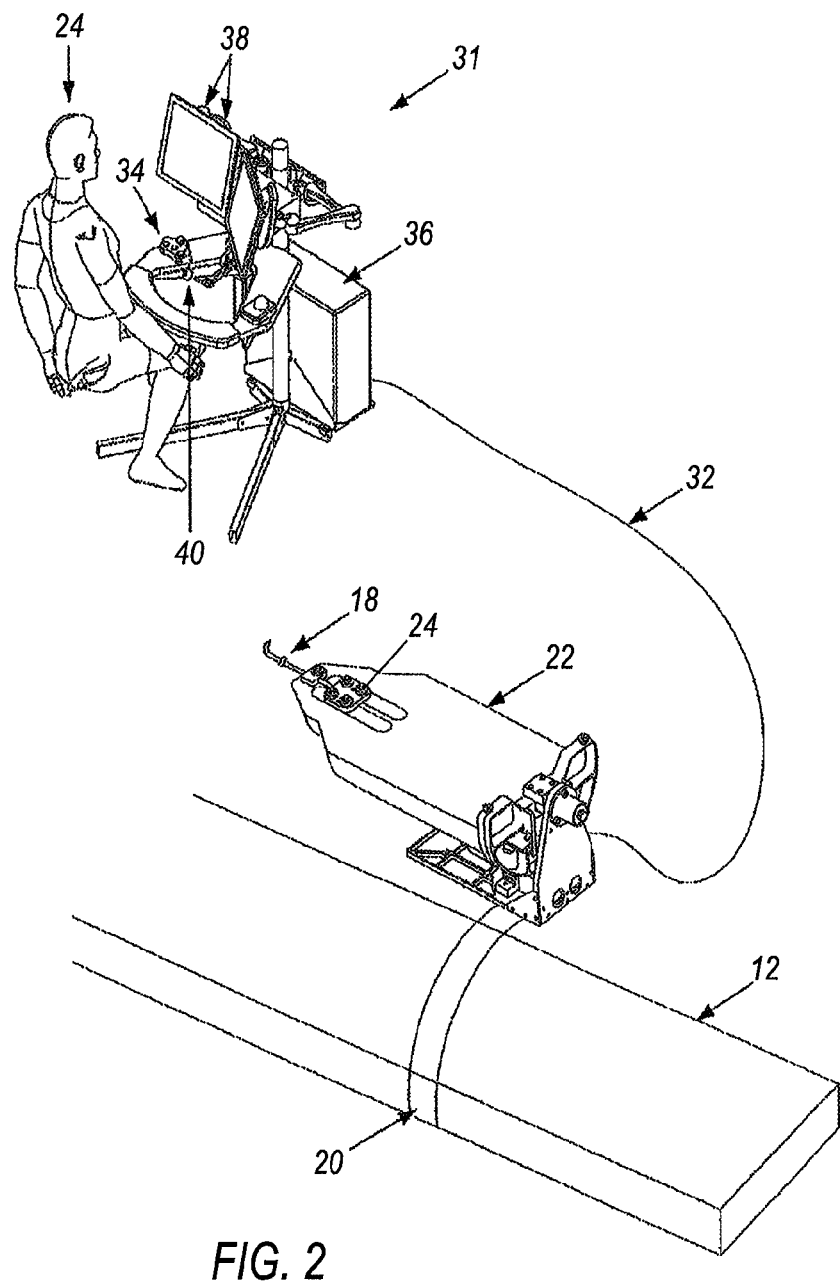
FIG. 2 illustrates an exemplary robotic surgical system.

Additional portions of the robotic surgical system 10 may be further seen in FIG. 2. More specifically, robotic surgical system 10 may further comprise an operator control station 31, which may be remotely positioned with respect to table 12. A communication link 32 transfers signals between the operator control station 31 and the RCM 22. The operator control station 31 includes a control console 34, a computer 36, a computer interface, such as a mouse, a visual display system 38 and a master input device 40. The master input device 40 may include, but is not limited to, a multi-degree of freedom device having multiple joints and associated encoders.

Figure 1B:
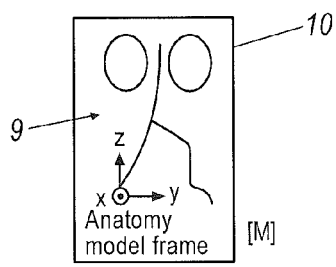
FIG. 1B illustrates a 3D Model frame.

Each element of the robotic surgical system 10 positioned within the operating suite may define a separate reference frame to which sensors may be localized. More specifically, separate reference frames may be defined for each of elements of the robotic surgical system 10. Such reference frames may include the following: a table reference frame TRF for the table 12, a setup joint frame SJF for the setup joint 20, an RCM reference frame RRF for the remote catheter manipulator (RCM) 22, a splayer reference frame SRF, a fluoroscopy reference frame FF. Separate reference frames may also be defined for a patient—patient reference frame PRR, a reference frame FRF for a sensor disposed within a surgical tool, and a pre-operative 3D frame AMF (best seen in FIG. 1B).

To relate a coordinate frame of a fiber optic sensor of a tool to either a fluoroscopy frame FF, or a pre-operative 3D frame AMF, a variety registration techniques is proposed herein. Generally, the techniques proposed herein fall into several categories. A first category involves using image processing or vision techniques to relate a reference frame RFR of a fiber sensor directly to an image or 3D model. This technique may be accomplished manually by a user or done automatically using image processing techniques. Another category to coordinate the reference frame FRF of a fiber optic sensor involves using knowledge about hardware, and potentially other sensors and or position of the fiber. Further discussion of these techniques is set forth below.

Registration to Fluoroscopy Coordinate Frame

Figure 3:
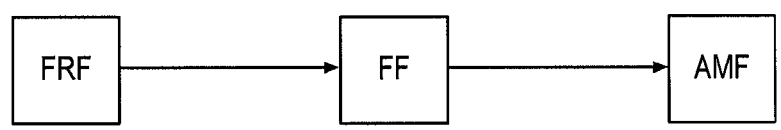
FIG. 3 is a schematic representation of a first registration technique of correlating a sensor reference frame to selective reference frames.

Referring to FIG. 3, the first category of registration techniques will now be described. The first category relates the coordinate system of the sensor reference frame FRF to a fluoroscopy reference frame FF directly. This technique utilizes fluoroscopy images taken during the surgical procedure by the fluoroscopy system 30, in real-time.

Figure 4:
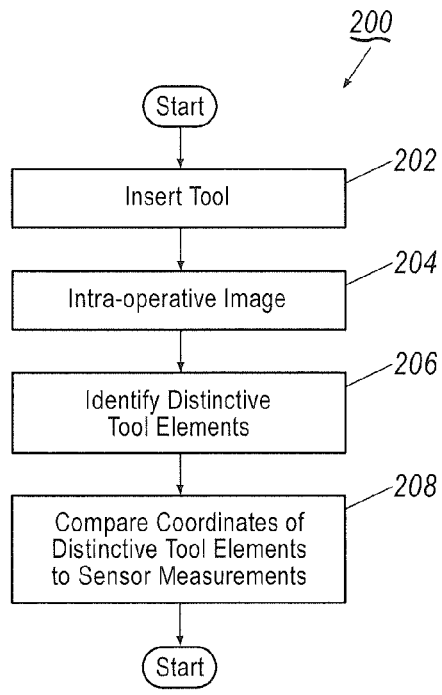
FIG. 4 is a flow chart that illustrates a method of transforming a reference frame for a sensor of a surgical tool into a target reference frame.

More specifically, an exemplary registration process 200 is illustrated in the flow chart of FIG. 4. The process 200 begins by inserting a tool 202 into a patient. As described above, in one exemplary configuration, the tool 202 is a catheter 18, which may be inserted by an RCM 22. Next, in step 204 an intra-operative image is taken of the tool 18.

In one exemplary arrangement, the intra-operative image is a fluoroscopy image taken by fluoroscopy system 30. Next, distinctive elements of the tool are identified in the fluoroscopy image in step 206. In one exemplary configuration, the identification step 206 may be accomplished by instructing the user to select certain marked points of a catheter 18 in the fluoroscopy image at the work station 31. Examples of marked points include, but are not limited to, physical features of the catheter 18 such as the tip of the catheter 18, certain shapes and an articulation band. In other exemplary configurations, fluoroscopy markers may be disposed on the catheter.

Once the selected points are identified in the fluoroscopy image, in the next step 208, coordinates of the selected points of the catheter 18 may be compared to corresponding measured points of elements of the catheter. In one exemplary configuration, measured points from a tool sensor operatively connected to the tool 18 may be used. More specifically, in one exemplary configuration, the tool sensor is a fiber optic sensor. Information about the fiber optic sensor will be known in relation to the features on the catheter from an in-factory calibration. This comparison can be used to determine a transformation matrix that can be used to transform a reference frame FRF for a sensor disposed within the surgical tool to into the fluoroscopy reference frame FF. This transformation then localizes the tool relative to the intra-operative fluoroscopy image.

Once the fiber sensor of the tool has been registered or localized to the fluoroscopy image, the tool operator can now move or drive the tool to various, desired points visualized in the fluoroscopy image. Moreover, the computer 36 may be configured to track the marked points over time, such that an appropriate transformation may be updated.

In one exemplary configuration, the identifiable markers need not be on the portion of the tool that is inserted into the patient. For example, markers may be embedded on a splayer 24, which may allow for larger and more complex markers to provide enhanced registration capabilities.

As described above, in addition to utilizing fluoroscopy marked points, it is also contemplated that distinct shapes that may be visible under fluoroscopy may also be used. However, this technique will require some image segmentation.

With respect to the proposed technique of localizing a sensor reference frame FRF to the fluoroscopy reference frame FF, the localization sensor could serve to reduce the use of fluoroscopy during a procedure. More specifically, use of fluoroscopy will only be required when re-registration appears to be required from the captured image and the data obtained from the sensor if the accuracy of the registration needs to be improved at any point during the procedure.

In certain arrangements, it may be desirable to further register the tool to a 3D model reference frame AMF, as illustrated in FIG. 3. Registration to the 3D Model is discussed more fully below.

Registration Through Successive Physical Components

Figure 5:
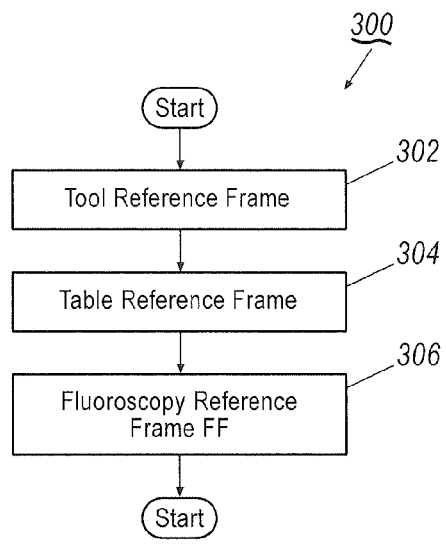
FIG. 5 is a flow chart that illustrates a method of transforming a reference frame associated with a tool into a target reference frame.

Another technique proposed to register a tool 18 to a desired reference frame involves the use of physical components of the medical system 10 and multiplying successive transformations. This proposed technique 300 is illustrated schematically in FIG. 5 and involves finding a transformation path from a tool reference frame such as a fiber sensor, splayer 24, or catheter 18, to the table 12, as in most surgical suite setups, the table location is generally known with respect to the fluoroscopy system 30. More specifically, registration technique 300 involves determining a tool reference frame 302 (where the tool reference frame may be defined as the sensor reference frame FRF, splayer reference frame SRF or a catheter reference frame) and correlating the tool reference frame to a table reference frame TRF in a second step 304, thereby registering the tool 18 to the table 12. Registering the tool 18 to the table 12 will serve to provide necessary information to permit registration to an additional target frame, such as a fluoroscopy reference frame FF, for example. Because the table 12 location is typically known with respect to a fluoroscopy system 30, once the tool 18 is registered to the table reference frame TRF, a comparison of set reference points of the table 12 with corresponding reference points in a fluoroscopy image may be used to determine a transformation matrix to transform the table reference frame TRF into the fluoroscopy reference frame FF. This transformation then localizes the tool relative to the intra-operative fluoroscopy image.

However, it is understood that the present disclosure does not require that the tool 18 be registered to the table 12. Indeed, it is expressly contemplated that registration of the tool 18 to other physical components within the surgical suite may also be utilized. This proposed technique requires the use of other sensors in addition to, or alternative to a fiber sensor, however. Exemplary configurations of registration through physical surgical suite components is are discussed in further detail below.

Figure 6:
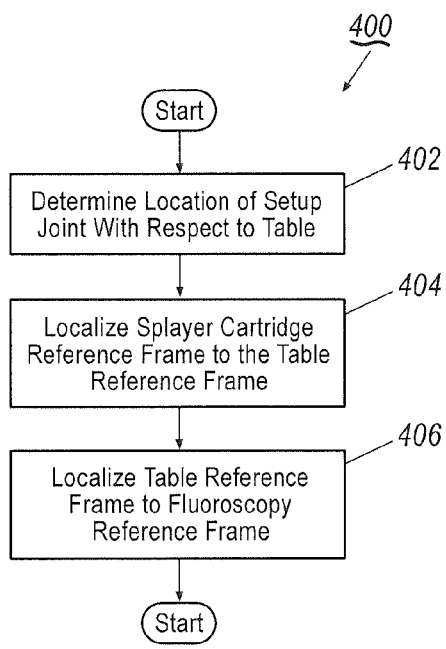
FIG. 6 is a flow chart that illustrates a method of transforming a reference frame associated with a tool into a target reference frame utilizing medical appliances.

One exemplary method of performing registration through successive physical components is illustrated in the flow chart in FIG. 6. In this technique, the registration process 400 begins with the step 402 of determining the location of the setup joint 20 with respect to the table 12. Encoders on the RCM 22 and setup joint 20, with kinematic models may be used to determine the location of the setup joint 20 with respect to the table 12. More specifically, the encoders assist with determining the location of the RCM 22 with respect to the table 12. With the location value of the position that the setup joint 20 is fixed to the table 12, the location of the splayer carriage 24 carried by the RCM 22 with respect to the table 12 can be determined; i.e., the setup joint reference frame SJF is localized with the RCM reference frame RRF. Because information about the catheter will be known in relation to the splayer carriage 24 from an in-factory calibration, in step 404 of the registration process 400, a comparison of the splayer carriage 24 information with the can be used to determine a transformation matrix that can be used to transform the splayer carriage reference frame SRF to the table reference frame TRF. As described above, because the table 12 location is known with respect to the fluoroscopy system 30, in step 406 another transformation may be done from the table reference frame TRF to the fluoroscopy reference frame FF. This final transformation, i.e., from the table reference frame TRF to the fluoroscopy reference frame FF, then localizes the tool relative to the intra-operative fluoroscopy image.

In another exemplary method of performing registration through successive physical components, inertial sensors on the RCM 22, coupled with the information about the initial position of the RCM 22 on the table 12, may be used to assist in localizing the catheter splayer reference frame SRF to the table reference frame TRF. More specifically, once the RCM 22 is localized to the table reference frame TRF, the catheter splayer reference frame SRF may be localized to the table reference frame TRF, as the position of the catheter splayer 24 with respect to the RCM 22 will be known from in-factory calibration.

Figure 7:
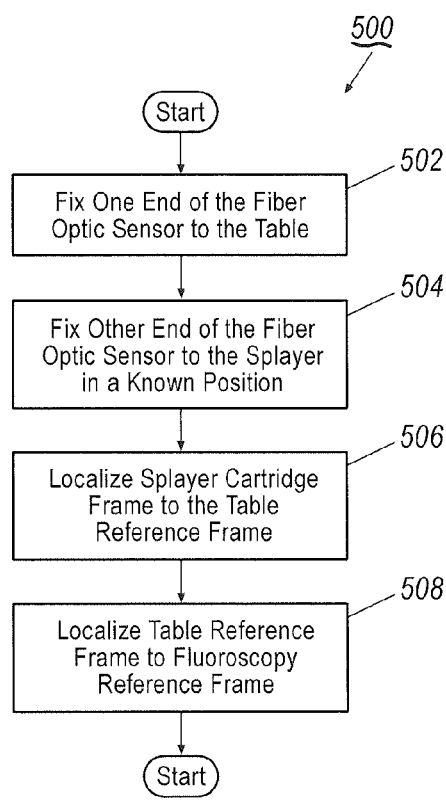
FIG. 7 is a flow chart that illustrates a method of using a sensor to transform a reference frame associated with a tool into a target reference frame.
Figure 8:
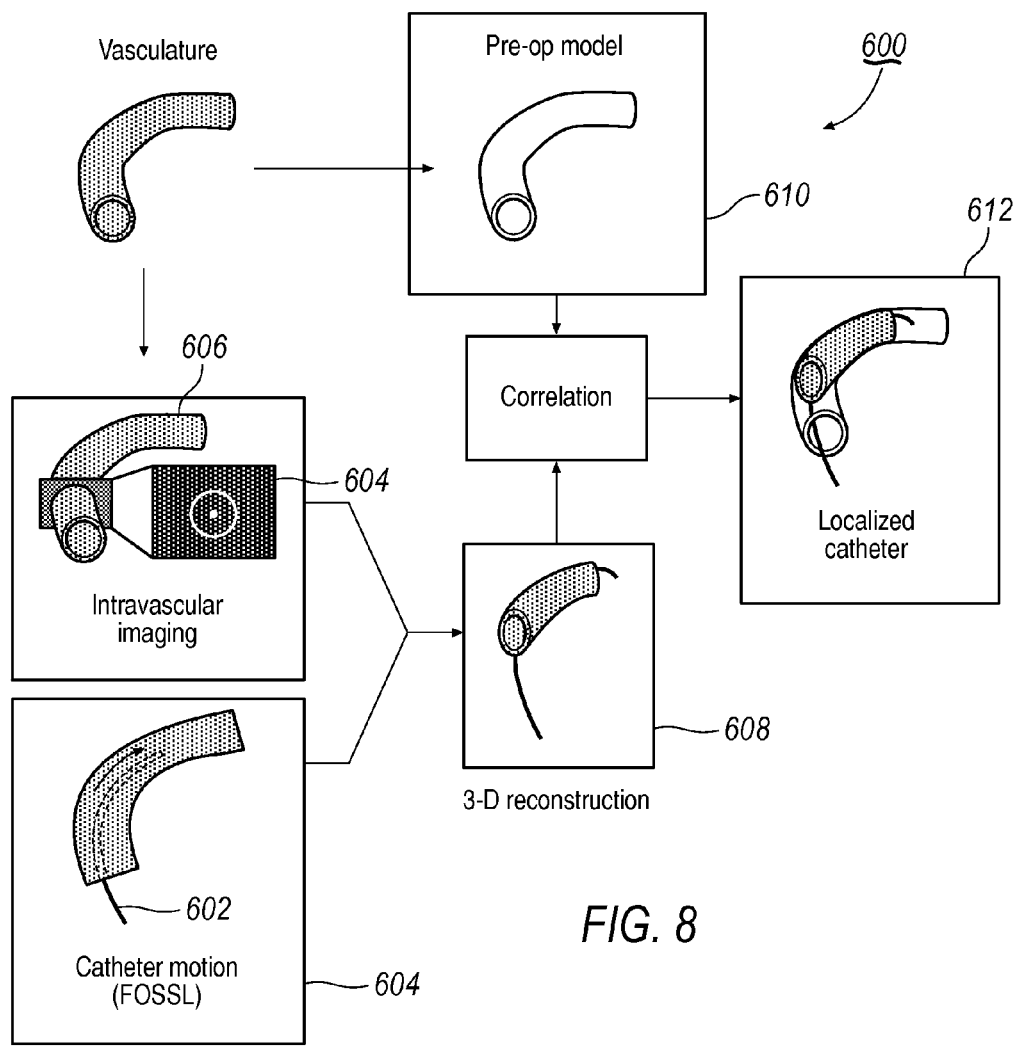
FIG. 8 is a schematic illustration of a method of using an intravascular imaging sensor coupled with a shape sensor to transform a reference frame associated with a tool into a target reference frame.

Yet another exemplary method 500 of performing registration through physical components is illustrated in FIG. 7. The method 500 uses a second fiber optic sensor. In a first step 502, one end of the fiber optic sensor is fixed to the table 12. Next, in step 504, the other end of the sensor is fixed to the splayer 24 in a known orientation/position. In this technique, a position and orientation transformation between the tip and base of the fiber sensor may be determined, thereby localizing the catheter splayer reference frame SRF to the table reference frame TRF in step 506. However, it is understood that the initial position of the fix point at the table must be known. Once the catheter splayer reference frame SRF is localized to the table reference frame TRF, because the table 12 location is known with respect to the fluoroscopy system 30, in step 508 another transformation may be done from the table reference frame TRF to the fluoroscopy reference frame FF. This final transformation, i.e., from the table reference frame TRF to the fluoroscopy reference frame FF, then localizes the tool relative to the intra-operative fluoroscopy image.

A further exemplary method of performing registration of a surgical tool to a physical component includes using electromagnetic sensors to track the location of the splayer 24 with respect to an electromagnetic sensor at a known location on the table 12. In using this technique, because the tool location is calibrated to the splayer 24 in the factory, once the splayer 24 is localized to the table reference frame TRF, the tool may be localized to the fluoroscopy reference frame FF as the table 12 is known with respect to the fluoroscopy system 30.

In yet another exemplary method, instead of electromagnetic sensors, overhead cameras or other visualization techniques may be employed to track distinct features on the splayer 24 and the table 12 to determine the respective orientation and position with regard to each other.

A further technique may use the range sensors (such as, e.g., IR or ultrasound) to find the distance to several distinct and predetermined points on the table 12 and the splayer 24. Once the splayer 24 is localized to the table reference frame TRF, the tool may be localized to the fluoroscopy reference frame FF as the table 12 is known with respect to the fluoroscopy system 30.

All of the above techniques serve to register the tool to a physical component within the surgical suite, such as, for example, the table 12. Some of the above techniques require the RCM 22 and setup joint 20 to be registered to the table 12. That pre-registration step may be achieved by using some known feature on the table 12 that the setup joint 20 may reference. In another exemplary configuration, the tip of a sensor equipped tool may be used to touch or register the known feature on the table 12 to locate the table 12 with respect to other equipment within the surgical suite.

The kinematics of the RCM 22 can also be calculated by holding the tip of a fiber optic equipped tool in an arbitrary fixed location and cycling through the various axes of the RCM 22. By keeping the tip in a fixed location, the relative changes to the fiber origin can be observed, and thus the kinematics of the system can be determined and localized to the table 12. Once localized to the table reference frame TRF, the tool may then be localized to the fluoroscopy reference frame FF, as discussed above.

In addition to adding the sensors discussed in the above techniques, additional modifications may be made to the location of the fiber base to facilitate registering the fiber sensor to the physical structure within the suite, such as, for example, the table 12. For example, one modification is to extend the length of a fiber in the catheter so that the origin/base can be extended out of the splayer 24 and attached to a fixture having a known location on the table 12. Once localized to the table reference frame TRF, the tool may then be localized to the fluoroscopy reference frame FF, as discussed above.

Registration to a 3D Model

Registration of the tool to a 3D Model is also contemplated in this disclosure. Such registration may be performed directly from the fiber sensor reference frame FRF to the 3D Model frame AMF. In one exemplary technique, the operator is utilized. When the tool (such as the catheter) is inserted into the patient, tortuosity can be visualized from the fiber sensor data, as well as on the pre-operative 3D Model. To register the tool in the 3D Model, the operator may translate and rotate the 3D Model so that distinct images and/or features in the tortuosity match or line up with the shape of the fibers. However, in using this technique, every time the patient moves, the tool should be re-registered.

In another exemplary arrangement, rather than have an operator manually match features in the tortuosity, in one technique, a computer algorithm such as automated geometric search or mathematical optimization techniques that segments the model and matches the model and tool shape dynamically may also be used to match various shapes or features from the fiber sensor to the 3D pre-operative Model. However, if the patient moves, even slightly, the 3D Model could be mis-registered. Thus, the algorithms may be used to re-register the tool automatically or the user could use an input device, such as a track ball or mouse to move the 3D Model manually.

Another proposed technique may be used to register the fiber sensor to the 3D Model through the fluoroscopy image, as illustrated in FIG. 3. In this technique, any of the above described techniques for registering the surgical tool 12 to the fluoroscopy reference frame FF may be utilized. To register the fluoroscopy reference frame FF to the 3D Model reference frame AMF, in one exemplary configuration, specific anatomical landmarks may be used to provide recognizable reference points. The only requirement for this approach is to have an anatomical landmark that is recognizable in both the fluoroscopy reference frame FF, as well as the pre-operative 3D Model reference frame AMF. Once the recognizable point is identified in the fluoroscopy image, the 3D Model may then by rotated by the operator to line up the recognized points in the fluoroscopy images with the 3D Model images. This action serves to register the fluoroscopy reference frame FF to the frame of the 3D Model AMF. As the tool has previously been localized to the fluoroscopy reference plane FF, so now once the fluoroscopy reference plane FF is so registered, the tool's location within the patient's anatomy may be determined with reference to the 3D Model. Thus, the tool is localized to the 3D Model. In one exemplary configuration, a visual representation to the tool, based on the transformation matrix, may be displayed on the 3D Model. In this manner, the tool operator may then navigate the tool through the 3D Model.

While certain of the above described techniques utilized distinct marked points of a tool, such as a medical catheter, to register the tool with the fluoroscopy image, it is also understood that registration of the tool may occur based on the location of the tool at the distinct anatomical landmarks. In other words, as the tip of the tool can be driven to a known anatomical location in the patient, the 3D Model may then be rotated by the user to overlay the known anatomical location in the 3D Model with the fluoroscopy image, in which the known anatomical location is visible. Such action will also serve to register the tool with the 3D Model or localize the tool in the reference frame of the 3D model reference frame AMF.

In another exemplary configuration, instead of, or in addition to, having the user manually rotate the 3D Model to correspond with the fluoroscopy image to line up distinct landmarks visible in both the fluoroscopy image and the 3D Model, the computer 36 may be programmed to employ a suitable algorithm such as automated geometric search or mathematical optimization techniques configured to match a distinct shape measured by the fiber sensor with a corresponding shape in the 3D Model. In this manner, the tool may also be registered with the 3D Model. The accuracy of this method will depend on the size of vessel that the tool is in, and the degree of curvature of the tool. Accuracy will be improved if the tool is in a smaller vessel and will be worse if the tool is in larger vessels. This automated technique can also be used in conjunction with the manual techniques described above. For example, the computer may be programmed to do automatic registration and suggest a preferred registration but the user may do final adjustments of the model. Once the tool is localized in the 3D Model of the patient's anatomy, the user may then proceed to maneuver the tool in the 3D Model.

Another technique that may be utilized to register the tool to the 3D Model through fluoroscopy system 30 involves the use of radiopaque markers. More specifically, radiopaque markers can be fixed to the anatomy. However, these markers would need to be present during pre-operative imaging when the 3D Model is created, and remain in the same location during intraoperative fluoroscopy imaging. With this technique, the position of these markers in the fluoroscopy reference frame FF can be used to correlate to the same markers in the 3D Model reference frame AMF, thereby registering the fiber sensor to the 3D Model reference frame AMF.

Another technique that may be utilized to register the surgical tool to a 3D Model utilizes intravascular imaging. This technique allows for 3D visualization of a surgical tool, such as, a catheter, in the anatomy, but without the use of fluoroscopic imaging. Such a technique can benefit both physicians and patients by improving the ease of tool navigation, as well as and reducing radiation exposure of personnel inside the operating room.

The registration technique 600 begins by utilizing a sensor 602 operatively coupled to the tool to sense a shape of the tool 604 while in the patient. This sensed shape is then mathematically correlated against features of the vascular model such as centerlines or walls in which a larger correlation value corresponds to a better match. The correlation can be performed in real-time on each shape or by batch processing a sequence of shapes. This proposed technique assumes that the tool will always follow a unique configuration through the vasculature, and thus, a global maximum for the correlation exists. However, the correlation may return many local maxima since the tool configuration may follow many different paths between fixed distal and proximal ends. Choosing an incorrect maximum introduces registration error. Furthermore, in some cases, the pre-operative 3D model may differ from the actual vasculature for a number of reasons, including, for example, patient motion or inaccuracies in pre-operative sensing. Such situations also may lead to registration error.

Recent advances in intravascular imaging technology have brought about sensors 604 that can provide information about the local structure of vessel walls 606. Such information may be used for shape registration and environmental mapping. Two examples of these sensors are intravascular ultrasound (IVUS) probes, and optical coherence tomography (OCT). Intravascular ultrasound periodically produces a 2-D cross-sectional view of the blood vessel either to the sides of the catheter in standard IVUS or to the front of a catheter in Forward-Facing IVUS. Optical Coherence Tomography periodically produces a local 3D view of the vessel into which the tool is inserted. The images produced by these technologies may be processed to provide an estimate of a curve or surface representing the vessel wall 606. The sensors 604 may also determine the location of the catheter's endpoint within the vascular cross-section. Use of the sensors coupled with the tool 602 to provide shape information coupled with information obtainable from sensors 604 configured to provide information about the vessel walls 606 can assist in defining the 3D shape of the blood vessel 608.

Once the shape of the vessel is defined or otherwise reconstructed using the combined sensor data, the shape can be mathematically correlated to the 3D model 610, thereby registering the tool to the 3D Model 612. In implementation, the 3D reconstruction and correlation steps may be combined into a single recursive filtering algorithm. A Bayesian filter (e.g. Extended Kalman Filter (EKF), Unscented Kalman Filter (UKF), or Particle Filter) may be used to develop an estimate of the tool's position relative to the pre-op 3D model given both imaging and sensor 602 information. The filter's state is a set of points or a parametric curve representing the position and shape of the tool 602 with respect to the pre-op 3D model, as well as the velocity of this shape. For accurate registration, patient motion may also be taken into account. Thus, the filter's state may also contains warping parameters for the pre-op 3D model. These warping parameters may be evenly distributed, or may be selected based on the structure of the anatomy around the vasculature. The motion of the structure of the anatomy around the vasculature may be measured using visible light tracking technologies such as stereoscopic cameras, structured light tracking technologies, and/or other localization technologies attached to the patient skin.

The recursive filtering algorithm operates by predicting the motion of the tool in the 3D model, then performing an update of the filter hypothesis given new sensor measurements. At each time-step, a kinematic model of the catheter and control inputs such as current pull-wire tension and displacement may be used to perform the filter's motion update. The filter's measurement update may apply a correction to the tool registration and model warping parameters by comparing a predicted vessel wall with the sensed position and orientation of the vessel from the imaging and sensor measurements. The update effectively executes the correlation between 3-D sensor information and the 3D model. Performing these correlations repeatedly in a recursive filtering framework may provide a real-time catheter position estimate. Furthermore, the filter's parameters may be tuned such that differences between the measurements and the model over a small time constant (ms) will lead to changes in the catheter position estimate in order to filter out high-frequency sensor noise. Differences over a large time constant (seconds) may lead to changes in the model's warping parameters.

Thus, once the tool has been registered to the 3D model, the location of the tool within the 3D model may be determined, allowing an operator to drive the tool within the vasculature using the 3D model without requiring intra-operative fluoroscopy.

Sensors 604 may also be utilized to sense the environment around the tool. Thus, once the tool is registered to the 3D the model, this environmental information, such as, for example, vascular occlusions may be displayed at the correct position in the 3D Model.

More specifically, after tool registration, the intravascular imaging sensor 604 provides a mechanism to sense and display features of the environment surrounding the tool without the use of fluoroscopy. There are many ways to display this information. One non-limiting option is to simply provide a display of a real-time view of the imaging sensor's output alongside a view of the catheter's location in the 3D model or superimposed on top of the 3D model. Another option may be to analyze the intravascular image to detect environmental changes. For example, IVUS image processing techniques can be used to detect areas of plaque in the image. This information can be used to annotate the IVUS image in order to alert the physician to environmental conditions. Since a combination of IVUS and sensor data 602 may provide 3D information on the structure of these plaque formations, the 3D pre-op model can also be annotated. In this way, the existing work that has used IVUS to perform vascular sensing may be leveraged by the combined IVUS and sensor system to provide a 3D view of the environment to the physician.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

While multiple embodiments and variations of the many aspects of the invention have been disclosed and described herein, such disclosure is provided for purposes of illustration only. Many combinations and permutations of the disclosed system are useful in minimally invasive medical intervention and diagnosis, and the system is configured to be flexible. The foregoing illustrated and described embodiments of the invention are susceptible to various modifications and alternative forms, and it should be understood that the invention generally, as well as the specific embodiments described herein, are not limited to the particular forms or methods disclosed, but also cover all modifications, equivalents and alternatives falling within the scope of the appended claims. Further, the various features and aspects of the illustrated embodiments may be incorporated into other embodiments, even if no so described herein, as will be apparent to those skilled in the art.

We claim:

1. A robotic system for manipulating a tool with respect to a 3D model of a blood vessel, where the tool comprises a shape sensor coupled thereto, the system comprising:

a robotic drive system comprising at least one actuator, the robotic drive system configured to couple with the tool to position the tool with respect to the 3D model, wherein the shape sensor on the tool senses a shape of the tool while in the blood vessel, and wherein the sensed shape of the tool in the blood vessel is correlated against features of the blood vessel in the 3D model; and a controller configured to compute a registration between a sensor reference frame and a 3D model reference frame such that the controller can direct the robotic drive system in the 3D model reference frame using the registration.

2. The robotic system of claim 1, wherein the controller is further configured to combine a plurality of discrete registrations to produce a combined registration between the sensor reference frame and the 3D model reference frame such that the controller can produce a plurality of signals to direct the robotic drive system in the 3D model reference frame using the combined registration.

3. The robotic drive system of claim 2, further comprising a master input device coupled to the controller, where the master input device uses the combined registration to permit intuitive driving of the tool using the robotic drive system.

4. The robotic drive system of claim 2, wherein the plurality of discrete registrations include at least a shape sensor to tool registration.

5. The robotic drive system of claim 2, wherein the plurality of discrete registrations comprise registering between a group selected from the shape sensor to tool, the tool to the 3D model, the tool to an operating room structure, the tool to the robotic drive system, the robotic drive system to the operating room structure, and the operating room structure to the 3D model.

6. The robotic drive system of claim 4, wherein the shape sensor to tool registration is specific to the tool.

7. The robotic drive system of claim 1, wherein the tool includes at least one optical fiber coupled thereto and where a shape sensor to tool registration is fixed.

8. The robotic drive system of claim 7, wherein the controller is further configured with an algorithm to match a curved shape of the tool determined by the fiber with a corresponding shape in an image.

9. The robotic drive system of claim 8, wherein the algorithm is one of an automated geometric search and a mathematical optimization technique.

10. The robotic drive system of claim 8, wherein the image is one of a pre-operative anatomical image and an intra-operative image.

11. The robotic drive system of claim 1, wherein the tool includes at least one electro-magnetic sensor coupled thereto and where a shape sensor to tool registration is fixed.

12. The robotic drive system of claim 2, wherein the plurality of discrete registrations includes a tool to robotic drive system registration.

13. The robotic drive system of claim 2, wherein the 3D model reference frame comprises a fluoroscopic model of the blood vessel, comprising a plurality of fluoroscopic images.

14. The robotic drive system of claim 13, wherein the plurality of discrete registrations includes a robotic drive system to fluoroscopic imaging device registration.

15. The robotic drive system of claim 13, wherein the plurality of discrete registrations includes a fluoroscopic imaging device to fluoroscopic image registration.

16. The system of claim 1, wherein the 3D model is derived from an imaging device.

17. The robotic drive system of claim 1, wherein the 3D model reference frame comprises the blood vessel in real time.

18. The robotic drive system of claim 2, wherein the plurality of discrete registrations further includes a robotic drive system to table registration and a table to patient registration.

19. The robotic drive system of claim 2, wherein the plurality of discrete registrations further includes a tool to table registration and a table to patient registration.

20. The robotic drive system of claim 2, wherein the combined registration further includes at least a position and orientation of at least one operating room structure.

21. The robotic drive system of claim 20, wherein the position and orientation of the at least one operating room structure is determined using a method selected from a group consisting of a direct measurement, a sensor, and a measurement using at least one image.

22. The robotic drive system of claim 2, wherein the combined registration further includes at least a position and orientation of at least the robotic drive system.

23. The robotic drive system of claim 2, wherein the combined registration further includes registration of a tool to at least one real time image of the 3D model.

24. The robotic drive system of claim 23, wherein the combined registration further includes pre-procedure image registration to the at least one real time image of the 3D model.

25. The robotic drive system of claim 23, wherein the tool to at least one real time image of the 3D model registration is registered one of manually, semi-automatically, and automatically.

26. The robotic drive system of claim 1, wherein the controller is further configured to update the registration to account for motion of the 3D model.

27. The robotic drive system of claim 1, wherein the controller is further configured to update the registration to account for motion of at least one operating room structure.

28. A system for controlling a medical device within a blood vessel in a patient for performing a procedure in the blood vessel, where the medical device comprises a shape sensor coupled thereto, the system comprising:
a user input device;
an actuator configured to manipulate and reposition the medical device with respect to a 3D model of the blood vessel, wherein the shape sensor on the medical device senses a shape of the medical device while in the blood vessel, and wherein the sensed shape of the medical device in the blood vessel is correlated against features of the blood vessel of the 3D model; and
a controller configured to convert a user input into a plurality of signals based on registration of a shape sensor reference frame to a patient reference frame.

29. The system of claim 28, wherein the patient reference frame is a reference frame of at least one image of an imaging device.

30. The system of claim 28, wherein the registration of the shape sensor reference frame to the patient reference frame further comprises registration of the shape sensor reference frame to a medical device reference frame and registration of the medical device reference frame to the patient reference frame.

31. The system of claim 28, wherein a pre-procedure registration is performed, the pre-procedure registration comprising registration of an imaging device with at least one image of the imaging device and registration of at least one medical appliance.

32. The system of claim 28, wherein registration of the shape sensor reference frame to the patient reference frame further comprises a shape sensor to image registration, comprising registration of the shape sensor reference frame to at least one real time image from an imaging device.

33. The system of claim 31, wherein the controller is further configured to update the pre-procedure registration by accounting for movement of the at least one medical appliance.

34. The system of claim 28, wherein the shape sensor is registered to the medical device and registration of the shape sensor to the medical device is specific to the medical device.

35. The system of claim 34, wherein the medical device includes at least one optical fiber coupled thereto, and wherein the shape sensor to medical device registration is fixed.

36. The system of claim 31, wherein the pre-procedure registration includes a medical device to actuator registration.

37. The system of claim 30, wherein the patient reference frame comprises reference frame in a fluoroscopic model of the patient comprising a plurality of fluoroscopic images.

38. The system of claim 28, wherein a plurality of discrete registrations are performed.

39. The system of claim 38, wherein the plurality of discrete registrations include an actuator to fluoroscopic imaging device registration and a fluoroscopic imaging device to fluoroscopic image registration.

40. The system of claim 28, wherein the patient reference frame comprises a reference frame in a virtual 3D model of the patient.

41. The system of claim 28, wherein the patient reference frame comprises a reference frame relative to a body of the patient in real time.

42. The system of claim 39, wherein a shape sensor to image registration includes an actuator to table registration and a table to patient registration.

43. The system of claim 42 wherein the shape sensor to image registration includes at least a position and orientation of at least one operating room structure.

44. The system of claim 43, wherein the position and orientation of the at least one operating room structure is determined using a method selected from a group consisting of a direct measurement, a sensor, and a measurement using at least one image.

45. The system of claim 32, wherein the shape sensor to image registration further comprises registration of a medical device to at least one real time image of the patient.

46. The system of claim 45, wherein the shape sensor to image registration further comprises a pre-procedure image registration to the at least one real time image of the patient.

47. The system of claim 45, wherein the medical device to at least one real time image of the patient registration is registered one of manually, semi-automated, and automatically.

48. The system of claim 32, wherein the controller is further configured to update the shape sensor to image registration to account for motion of the patient.

49. The system of claim 28, wherein the controller is further configured to update the shape sensor to the patient reference frame registration to account for motion of at least one operating room structure.

50. The robotic system of claim 1, further comprising a second sensor coupled to the tool, wherein the second sensor is configured to sense a structure of a patient's anatomy.

51. The robotic system of claim 50, wherein the controller is configured to combine the sensed structure of the patient's anatomy with the registration of the sensor reference frame to produce a combined registration between the sensor reference frame and the 3D model reference frame.

* * * * *